United States Patent

Garner

[11] 3,989,702
[45] Nov. 2, 1976

[54] FLAME RETARDANT

[75] Inventor: Albert Y. Garner, Yellow Springs, Ohio

[73] Assignee: Monsanto Research Corporation, St. Louis,, Mo.

[22] Filed: July 22, 1974

[21] Appl. No.: 490,607

[52] U.S. Cl. ............ 260/249.6; 106/15 FP; 260/551 P; 427/342; 427/390 D; 427/392; 428/274; 428/296
[51] Int. Cl.² ............ C07D 251/66; C09K 3/28
[58] Field of Search ............ 260/551 P, 249.6

[56] References Cited
UNITED STATES PATENTS

| | | | |
|---|---|---|---|
| 2,782,133 | 2/1957 | Vallette | 106/15 FP X |
| 3,050,522 | 8/1962 | Coates et al. | 260/249.6 |
| 3,296,265 | 1/1967 | Garner | 260/249.6 |
| 3,787,407 | 1/1974 | Hendricks | 260/249.6 |
| 3,887,553 | 6/1975 | Nachbier et al. | 260/249.6 |

FOREIGN PATENTS OR APPLICATIONS

| | | | |
|---|---|---|---|
| 1,114,181 | 9/1961 | Germany | 260/249.6 |

OTHER PUBLICATIONS

"Derivatives of Trichlorophosphazo–1,3,5–triazines," Derkach et al., CA 69:36082s, (1968).
"Fireproofing of Synthetic Fibers . . . ", Date et al., CA 78: 137898d (1973).
"Phosphorus–Containing Condensates as Flame Retardants," Nachbur et al., CA 79:93396c, (1973).

Primary Examiner—Floyd, D. Higel
Assistant Examiner—Thomas A. Waltz
Attorney, Agent, or Firm—Bruce Stevens

[57] ABSTRACT

Mixtures comprising compounds of the formula

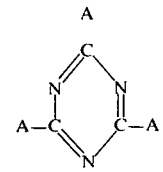

wherein A is either $NH_2$ or $N=P(NH_2)_3$, provided at least one A is $N=P(NH_2)_3$, have been found to be good flame-retardants for material made from cotton or polyester-cotton having about 30 to 70% by weight cotton. Conveniently the material can be treated with an aqueous solution containing a sufficient amount of said mixtures and the material dried to make the material self extinguishing. Then the treated and dried material is cured at a sufficient temperature to bond said compounds to the material. Alternatively and usually preferably the drying and curing can be accomplished as a single operation.

1 Claim, No Drawings

FLAME RETARDANT

BACKGROUND OF THE INVENTION

1. Field of the Invention

Fireproofing.

2. Description of the Prior Art

One of the older patents in this art is U.S. Pat. No. 2,782,133 teaching aminocyclophosphazene as a fireproofing agent for cellulosic fibers such as cotton. A recent patent is U.S. Pat. No. 3,711,542 teaching certain new N-methylol phosphazene compounds as flame retardants on cotton, and this patent under Background of the Invention contains a summary of certain phosphazene prior art on flameproofing.

SUMMARY OF THE INVENTION

Mixtures comprising compounds of the formula

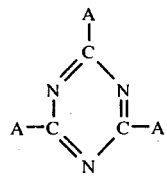

wherein A is either $NH_2$ or $N=P(NH_2)_3$, provided at least one A is $N=P(NH_2)_3$, have been found to be good flameretardants for material made from cotton or polyester-cotton having about 30 to 70% by weight cotton. Conveniently the material can be treated with an aqueous solution containing a sufficient amount of said mixtures and the material dried to make the material self extinguishing. Then the treated and dried material is cured at a sufficient temperature to bond said compounds to the materials. Alternatively and usually preferably the drying and curing can be accomplished as a single operation.

DESCRIPTION OF THE PREFERRED EMBODIMENTS

Preparation of the flame-proofing reagents — Melamine and phosphorus pentachloride were allowed to react in molar ratios of 1/3; 1/2; 1/1. After reaction with ammonia, three materials were obtained having different solubilities, although their infrared spectra were quite similar. Elemental analyses showed that these materials were not pure compounds nor were they the simple materials expected by the reaction of the trihalophosphazenes with excess ammonia.

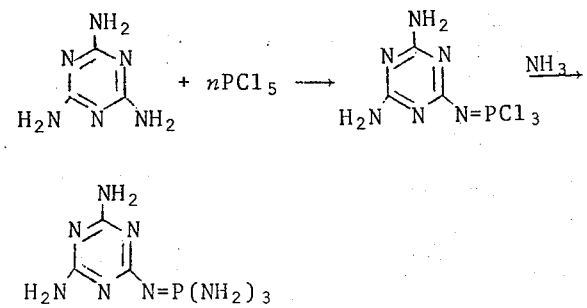

$n = 1, 2,$ or $3$, but $n = 1$ in the above reaction.

A reference to the tris-trichlorophosphazene was found in the literature (I. Derkash, USSR 168,693, C.A. 63, 1700g; C.A. 69, 36082s); however, no reference to any of the ammoniated compounds from melamine $+PCl_5 + NH_3$ has been found. All of the ammoniated products were water soluble and contained chlorine. Recrystallization from water resulted in losses of chlorine and significant changes in the phosphorus analyses. These products flame retarded cotton and 65/35 polyester-cotton.

The reaction of 3 moles of phosphorus pentachloride and a mole of melamine will be used to represent all of the reactions between these two reagents in varying stoichiometries.

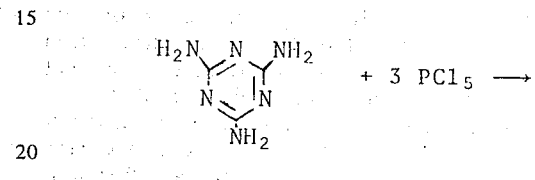

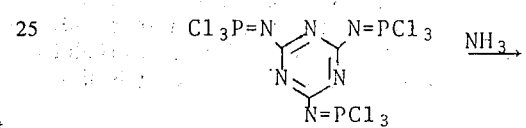

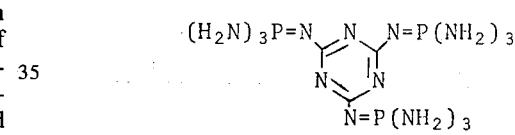

A mixture of 30.0 g (0.24 m) of melamine (MCB) and 177.5 g (0.85 m) of $PCl_5$ with 200 ml of $CHCl_3$ was heated at gentle reflux with stirring, until the evolution of HCl had ceased (44 hours). The top of the condenser was protected by a Drierite tube. The mixture was allowed to cool, and the solvent and trapped HCl were removed on a rotary evaporator leaving 190.7 g of a white solid which smelled of $CHCl_3$. The solid was reactive to water but was not as reactive as $PCl_5$.

The solid was placed in a 3-liter flask with 500 ml of toluene. Eight hundred ml of liquid ammonia was added in portions. A Dry Ice condenser was used to contain the ammonia. This mixture was stirred overnight. The copious white solid that had formed was filtered to remove the toluene. Twelve hundred ml of ammonia was poured cautiously over the filter cake. The solid left on the filter and the solid left after evaporation of the ammonia from the filtrate had identical infrared spectra indicating the presence of both product and ammonium chloride and that the product was soluble in ammonia. The residue from evaporation of the ammonia filtrate was added to the filter cake giving a combined weight of product of 230 g. The product was soluble in water. The mixture was also soluble in methanol and ethanol and formed a salt with acetic acid. There was no apparent solubility in acetone, acetonitrile, THF, benzene, toluene, chloroform or methylene chloride.

The 230 g of solids product was slurried in 1200 ml of chloroform and 315 ml (3 m) of diethylamine. The mixture was heated slowly to reflux. (This method, see below, affords a chloroform soluble amine hydrochloride from the ammonium chloride, thus enabling separation of the phosphazene.)

$$(C_2H_5)_2NH + NH_4Cl \rightarrow (C_2H_5)_2NH_2Cl + NH_3$$

The ammonia was detected at the top of the condenser. The mixture was refluxed overnight. The cooled solution was filtered to remove the red chloroform solution of the amine hydrochloride. The filter cake product was washed with chloroform and air dried, wt. 89.9 g. The infrared spectrum of this product showed no ammonium chloride. An aqueous solution of the product was neutral; however, there was a slight indication of chloride ion using a silver nitrate test.

When heated in a capillary tube, gas was evolved at 113° C to form a foam; at 260° C, more expansion occurred and at 280°–300° C, the material softened to a thick syrup with more gas evolution. A thermogravimetric analysis on this material in air from room temperature to 980° C left 18% residue. At 300° C, only 20% of the material had decomposed. Another 30% was lost between 300° and 500° C. There was slightly less weight loss in helium. An elemental analysis of the product was as follows:

| % | Found |
|---|---|
| C | 10.17 |
| H | 5.61 |
| N | 41.04 |
| P | 19.06 |
| Cl | 1.70 |

Treatment of Fabrics — A solution containing the desired weight percent of the flameproofing reagent in sufficient water to just saturate the cloth was poured on a weighed piece of cloth lying flat in a plastic bag. The solution was worked over the surface of the cloth, until it was uniformly wet. After standing for about 15 minutes, the cloth was placed in an oven at the desired temperature and cured. After curing and drying, the cloth was allowed to equilibrate before being weighed.

Cure Conditions — Cure was effected at 140° C or as shown in the following table using the one operation to also dry the wet sample. Formaldehyde or trimethylolmelamine and quarternary base, sodium hydroxide or magnesium chloride were included as auxiliary treatments in some instances attempting to make the material more durable to washing, and these auxiliary agents are present in the same aqueous solution as the primary reagent when it is applied to the material.

Flammability Tests — Samples of cloth 10 in. × 3½ in. were clamped in a metal stand and tested according to AATCC Test Method 34-1969 using a propane torch in place of the special gas mixture. This flammability test is described in J. Amer. Assoc. Text. Chem. and Colorists 2 (3), 49/19 (1970).

Tabulation of Data — The test data are tabulated in the following table. The table is divided into three main sections: Fabric Treatment, Flammability Tests and Miscellaneous Conditions. The following column headings are used. The added notes are for explanation of their meanings where not self explanatory.

| Column | Heading | Explanation |
|---|---|---|
| 1 | Cloth Type | |
| 2 | Reagent | *Melamine/PCl₅ + NH₃ product |
| 3 | Auxiliary | material used to bind to cloth such as formaldehyde and catalyst; QB = quarternary base, TMM = trimethylolmelamine |
| 4 | % Final Add-On | weight percent of product added to the cloth after all processes including laundering if indicated in column 9 |
| 5 | Distance Burned, in. | this represents the length of the sample that was burned out, charred or scorched from the ignited edge |
| 6 | Time, Sec | time from ignition to removal of flame even though self extinguishment had already occurred |
| 7 | (SE) Self Extinguish | answers question — Did the fire self extinguish before burning the entire sample length? Y = yes; N = no |
| 8 | Cure Temperature | temperature at which the wet cloth was dried and cured in a single operation |
| 9 | Post Treatment | indicates treatment of sample after curing but before flammability test. L = Laundered, detergent wash and dried; NL = Not Laundered |

| | Fabric Treatment | | | Flammability Test | | | Miscellaneous Conditions | |
|---|---|---|---|---|---|---|---|---|
| Cloth Type | Reagent | Auxiliary | % Final Add-On | Distance Burned, in. | Time, Sec | SE | Cure Temp ° C | Post Treatment |
| cotton | — | — | 0.00 | 10 | 1 | N | — | NL |
| 65/35 polyester/cotton | — | — | 0.00 | 10 | 1 | N | — | NL |
| cotton | * | — | 5.27 | 3½ | 3, 15 | Y | 120 | NL |
| cotton | * | — | 5.27 | 10 | 3 | N | 120 | L |
| 65/35 polyester/cotton | * | — | 15.2 | 4 | 3 | Y | 140 | NL |
| 65/35 polyester/cotton | * | — | 15.2 | 10 | 3 | N | 140 | L |
| cotton | * | — | 2.5 | 5½ | 12 | Y | 150 | NL |
| cotton | * | — | 2.5 | 10 | 15 | N | 150 | L |
| 65/35 polyester/cotton | * | — | 9.3 | 6 | 15 | Y | 150 | NL |
| 65/35 polyester/cotton | * | — | 9.3 | 10 | 15 | N | 150 | L |
| 65/35 polyester/cotton | * | CH₂O | 4.45 | 10 | 8 | N | 120 | L |
| cotton | * | CH₂O, Q.B.¹ | 20.3 | 3 | 20 | Y | 130 | NL |
| cotton | * | CH₂O, Q.B. | 14.7 | 6 | 15 | Y | 130 | L |
| 65/35 polyester/cotton | * | CH₂O, Q.B. | 30.7 | 3 | 20 | Y | 130 | NL |

-continued

| Cloth Type | Fabric Treatment Reagent | Auxiliary | % Final Add-On | Flammability Test Distance Burned, in. | Time, Sec | SE | Miscellaneous Conditions Cure Temp °C | Post Treatment |
| --- | --- | --- | --- | --- | --- | --- | --- | --- |
| polyester/cotton 65/35 | | | | | | | | |
| polyester/cotton | * | CH₂O, Q.B. | 0 | 10 | 15 | N | 130 | L |
| cotton | * | CH₂O, NaOH | 7.7 | 10 | 10 | N | 140 | L |
| 65/35 | * | CH₂O, NaOH | 6.45 | 8 | 8 | N | 140 | L |
| polyester/cotton cotton | * | Q.B. | 5.7 | 10 | 5 | N | 140 | L |
| 65/35 | * | Q.B. | 6.25 | 10 | 5 | N | 140 | L |
| polyester/cotton cotton | * | TMM²,Q.B. | 6.4 | 4 | 5–30 | Y | 140 | L |
| 65/35 | * | TMM, Q.B. | 8.9 | 10 | 5 | N | 140 | L |
| polyester/cotton 65/35 | * | TMM, Q.B. | 9.5 | 10 | 10 | N | 140 | L |
| polyester/cotton 50/50 | * | TMM, Q.B. | 20.0 | 4½ | 3 | Y | 140 | NL |
| polyester/cotton 50/50 | * | TMM, Q.B. | 7.6 | 10 | 10 | N | 140 | L |
| polyester/cotton 65/35 | * | CH₂O, Q.B. | 3.85 | 10 | 8 | N | 140 | L |
| polyester/cotton 65/35 | * | TMM, Q.B. | 10.7 | 10 | 15 | N | 140 | L |
| polyester/cotton 65/35 | * | CH₂O, MgCl₂ | 4.86 | 10 | 10 | N | 140 | L |
| polyester/cotton cotton | * | CH₂O, MgCl₂ | 7.1 | 10 | 10 | N | 140 | L |

¹Quaternary base
²Trimethylol melamine
*Melamine/PCl₅ + NH₃
SE = Self Extinguishing
Y = Yes
NL = Not Laundered
N = No
L = Laundered
Note: Untreated cotton and polyester/cotton cloth are not self extinguishing in the flammability test and data for these materials are given for comparison purposes.

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. For example, although mixtures of compounds of the invention were used for flameproofing, each individual compound is a flameproofing agent, i.e. each compound whether one, two or all three A's of the general formula is N=P(NH₂)₃. Accordingly, modifications are contemplated which can be made without departing from the spirit of the described invention.

What I claim is:
1. A mixture comprising compounds of the formula

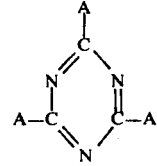

wherein A is NH₂ or N=P(NH₂)₃, provided at least one A is N=P(NH₂)₃.

* * * * *